United States Patent [19]
Coleman

[11] Patent Number: 5,840,278
[45] Date of Patent: Nov. 24, 1998

[54] NASAL SPRAY HAVING A MINERAL VITAMIN COMPONENT, A MINERAL COMPONENT AND ALOE VERA

[76] Inventor: Thomas Coleman, 9536 Wilshire Blvd. #410, Beverly Hills, Calif. 90212

[21] Appl. No.: 803,535

[22] Filed: Feb. 20, 1997

[51] Int. Cl.$^6$ ...................................................... A61K 9/12
[52] U.S. Cl. ........................ 424/45; 424/195.1; 424/639; 424/682; 424/722; 424/641
[58] Field of Search .............................. 424/45, 602, 639, 424/641, 665, 195.1, 682, 722, 464.1

[56] References Cited

U.S. PATENT DOCUMENTS 4,983,595  1/1991  Benjamin et al. ...................... 514/174

OTHER PUBLICATIONS

Gennaro, A.R. (1985). Remington's Pharmaceutical Sciences. Mack Pub. Co., PA., p. 1500.

Ansel, H.C. et al. (1995). Pharmaceutical Dosage Forms and Drug Delivery Systems. Williams & Wilkens. pp. 415–418.

Product Alert, vol. 25, No. 34 (1995).

CA 118:16335 (1992).

CA 102:191255 (1985).

*Primary Examiner*—Raj Bawa
*Attorney, Agent, or Firm*—Evan M. Kent, Esq.; Russ, August & Kabat

[57] ABSTRACT

An aqueous nasal spray formulation contains a vitamin component, a mineral component, a aloe vera in a water based solvent. The vitamin component contains Vitamin C, Rose Hips, Acerola, Lemon Bioflavanoids, Hesperidin, Rustin and Vitamin $B_6$. The mineral component contains potassium, calcium, magnesium, zinc and manganese. In the formulation, the vitamin component accounts for 25–40% by volume of the formulation, the mineral component is from 11–12% by volume and the aloe vera is from 8–12% by volume of the formulation.

6 Claims, No Drawings

NASAL SPRAY HAVING A MINERAL VITAMIN COMPONENT, A MINERAL COMPONENT AND ALOE VERA

BACKGROUND OF THE INVENTION

The invention pertains to an aqueous formulation that is dispensed as a nasal spray that functions as a cold virus remedy.

The unique combination of vitamins, minerals and aloe vera dispensed as an aqueous non-aerosol mist provides rapid and enhanced relief to the user in an easy dispensing format.

SUMMARY OF THE PRESENT INVENTION

The formulation of the present invention includes an unique combination of vitamins, minerals and aloe vera in an aqueous solution. The unique formulation is designed to be dispensed as a nasal mist.

DETAILED DESCRIPTION OF THE PREFERRED EMBODIMENT

The unique Vitamin Component of the formulation includes a large proportion of powdered buffered vitamin C (Ascorbate); Rosa Hips; Acerola; Lemon Bioflavonoids; Rustin, Hesperidin and Vitamin $B_6$. This component makes up roughly from 25 to 40% by volume of the formulation.

The unique Mineral Component of the formulation includes Zinc (from chelated Zinc Gluconate or Zinc Picolinate); Potassium; Calcium; Magnesium; and Manganese. This component makes up roughly from 8 to 12% by volume of the formulation.

Further contained in the aqueous formulation is approximately 8 to 12% by volume aloe vera.

The solvent or water component is roughly 45–60 volume percent of the formulation and contains some sodium bicarbonate and benzyl alcohol therein.

According to the preferred embodiment of this invention, a particular preferred composition for a nasal spray is an follows:

Total Volume 1.5 Fluid oz. (44 mm)

Solvent Volume: 0.8 fluid oz.
Purified Water
Sodium Bicarbonate (Sodium Chloride 0.65%)
Benzyl Alcohol Vitamin Component Volume: 0.5 fluid oz.

4,000 mg Powdered Vitamin C (Ascorbate) Buffered
1,170 mg Rose Hips
800 mg Acerola
1,000 mg Lemon Bioflavonoids
50 mg Rustin
50 mg Hesperidin
50 mg Vitamin $B_6$ Mineral Component Volume: 0.15 fluid oz.

120 mg Potassium
106 mg Calcium
54 mg Magnesium
35 mg Zinc
0.5 mg Manganese

Aloe Vera Component Volume: 0.15 fluid oz.

What is claimed is:

1. An aqueous nasal spray formulation consisting essentially of: 25–40% by volume of a vitamin component blend consisting of vitamin C, rose hips, acerola and lemon bioflavenoids; 8–12% by volume of a mineral component blend consisting of zinc, potassium, calcium and magnesium; 8–12% by volume aloe vera and 45–60% by volume of a water-based solvent.

2. The aqueous nasal spray formulation as claimed in claim, wherein said water-based solvent is selected from the group consisting of sodium bicarbonate and benzyl alcohol.

3. An aqueous nasal spray formulation consisting essentially of: 25–40% by volume of a vitamin component blend consisting of vitamin C, rose hips, acerola, vitamin $B_6$, rustin, hesperidin and lemon bioflavenoids; 8–12% by volume of a mineral component blend consisting of zinc, potassium, calcium and magnesium; 8–12% by volume aloe vera and 45–60% by volume of a water-based solvent.

4. An aqueous nasal spray formulation consisting essentially of: 25–40% by volume of a vitamin component blend consisting of vitamin C, rose hips, acerola and lemon bioflavenoids; 8–12% by volume of a mineral component blend consisting of zinc, potassium, calcium, manganese and magnesium; 8–12% by volume aloe vera and 45–60% by volume of a water-based solvent.

5. The aqueous nasal spray formulation as claimed in claim 3, wherein said vitamin component contains:

4,000 mg vitamin C;
1,170 mg rose hips;
800 mg acerola;
1,000 mg lemon bioflavenoids;
50 mg hesperidin;
50 mg rustin; and
50 mg vitamin $B_6$.

6. The aqueous nasal spray formulation as claimed in claim 4, wherein said mineral component contains:

120 mg potassium;
106 mg calcium;
54 mg magnesium;
35 mg zinc; and
0.25 mg manganese.

* * * * *